United States Patent [19]
Hirschenbain

[11] Patent Number: 5,483,975
[45] Date of Patent: Jan. 16, 1996

[54] DEVICE FOR EQUALIZING PRESSURE ACROSS THE EARDRUM OF DIVERS

[76] Inventor: Aviv Hirschenbain, 8 Emanuel Haromi, 62645 Tel Aviv, Israel

[21] Appl. No.: 402,226

[22] Filed: Mar. 10, 1995

[51] Int. Cl.⁶ ................................................ A61F 11/00
[52] U.S. Cl. ................................... 128/864; 128/866
[58] Field of Search ............................ 128/845, 846, 128/864, 865, 866, 867, 206.26, 207.11, 201.29; 2/2.14, 2, 428

[56] References Cited

U.S. PATENT DOCUMENTS

| | | | |
|---|---|---|---|
| 20,834 | 7/1858 | Ware | 128/866 |
| 1,324,747 | 12/1919 | Runyan | 128/207.11 |
| 2,476,589 | 7/1949 | Driskill | 128/866 |
| 2,488,235 | 11/1949 | Pfeiffer | 2/428 |
| 3,018,776 | 1/1962 | Suitta | 128/206.26 |
| 4,896,380 | 1/1990 | Kamitani | 2/428 |

Primary Examiner—Michael A. Brown
Attorney, Agent, or Firm—Mark M. Friedman

[57] ABSTRACT

A device for facilitating the equalization of pressure across the eardrum of a user which typically includes a facemask configured to fit over at least the eyes and nose of the user. The device further includes a strap for securing the facemask to the face of the user. The strap, when secured to the head of the user, defines a single air space which includes ear portions overlying the user's ears and a connecting portion overlying the sides and back of the user's head and connecting the ear portions. Finally, the device includes a tube for supplying air to the air space. One end of the tube is connected to the air space while the other end of the tube is connected to a source of pressurized air, such as the facemask, the air supply controller or the air supply mouthpiece.

12 Claims, 4 Drawing Sheets

DEVICE FOR EQUALIZING PRESSURE ACROSS THE EARDRUM OF DIVERS

FIELD AND BACKGROUND OF THE INVENTION

The present invention relates to underwater diving equipment and, more particularly, to devices for facilitating the equalization of pressure between the diver's middle and outer ear.

As shown in FIG. 1, the human ear is made up of three sections, commonly designated the outer ear, the middle ear and the inner ear. The outer ear includes the portion of the ear from the eardrum 10 outward to the ear opening. The inner ear includes the cochlea 12 and the three semi-circular canals 14. The middle ear is that portion of the ear between the eardrum 10 and the inner ear.

The middle ear is connected to the mouth cavity (not shown) through the eustachian tube 16, whose chief function is to equalize the pressure between the middle ear and the mouth cavity (typically the ambient pressure). Thus, under normal conditions, whenever the ambient pressure rises, the pressure in outer ear rises, as does the pressure in the mouth cavity. The rise in pressure in the mouth cavity brings about a concomitant rise in the middle ear through the eustachian tubes. The result is adequate pressure equalization between the outer and middle ear across the eardrum (see FIG. 2).

The pressure equalization is particularly important for divers since the ambient pressure changes dramatically and rapidly as the diver lowers himself beneath the water surface or rises toward the water surface.

The pressure equalization may be delayed or prevented when secretions block the eustachian tubes (see FIG. 3). This may be the case when the diver's eardrum is excited by low temperatures, water or pressure which brings about edema with its excessive secretion from the mucous membranes surrounding the middle ear and the eustachian tube. The edema furthermore narrows the eustachian tubes.

Furthermore, when diving the pressure on the outer ear increases almost instantaneously while the pressure in the middle ear increases at a lower rate, because of the narrowness of the eustachian tubes, which causes, for a short time, a relative under-pressurized condition in the middle ear. This under-pressure can stimulate the secretion of mucous and blood from the tissue surrounding the middle ear and eustachian tube and could lead to the blockage of the eustachian and the prevention of further pressure stabilization.

The result of a pressure differential between the outer and middle ear can vary from discomfort to great pain and could, in some cases, lead to the rupture of the eardrum.

Additionally, it is desirable to prevent the entry of cold water into the ear, which could result in loss of balance, stimulated ear mucous and blood secretions and bacterial infections.

To prevent the pressure equalization and related difficulties, it has been proposed to prevent entrance of water into the ear and to provide external tubes which functionally supplement the eustachian tubes and which serve to equalize the pressure across the eardrum.

U.S. Pat. No. 4,896,380 discloses a facemask which is equipped with a pair of tubes. Each tube features an earplug at its far end. Each of the earplugs can be plugged into the ear canal and air from the facemask is able to reach the outer ear through the tube in order to equalize the pressure across the eardrum. A disadvantage of such a system is that the air pressure from the mask is transferred directly to the outer ear without any delay or attenuation which could cause the user considerable discomfort. In addition, the earplugs tend to get dislodged from the ears during a dive, which leads to loss of air and discomfort. A further disadvantage is that a blockage of one of the tubes could create a significant pressure difference in the two ears which could greatly inconvenience the diver.

U.S. Pat. No. 2,488,235 also discloses an underwater facemask equipped with a pair of tubes. Each tube communicates at its far end with a substantially semi-spherical ear cup which covers the user's ear. The strap of the facemask serves to push the ear cups toward the user's ears. A disadvantage of such a system is that the strap securing the facemask to the face of the diver and the ear cups are essentially separate units so that the strap exerts inward pressure on the ear cups without relation to the ambient water pressure which destroys any chance of fine tuning the pressure on the user's ears, as described below. A further advantage is that the use of a pair of tubes makes it possible for one tube to get blocked which would create a pressure difference in the two ears with adverse consequences for the diver.

There is thus a widely recognized need for, and it would be highly advantageous to have, a simple and reliable device which will aid divers by equalizing the pressure between the outer and middle ear and between the two ears of the diver in a way which will minimize or eliminate discomfort.

SUMMARY OF THE INVENTION

According to the present invention there is provided a device for facilitating the equalization of pressure across the eardrum of a user, comprising: (b) a strap, at least a portion of the strap, when the strap is secured to the head of the user, defining a single air space, the air space including ear portions overlying the user's ears and a connecting portion overlying the sides and back of the user's head and connecting the ear portions; and (c) a tube for supplying air to the air space, a first end of the tube being connected to the air space and a second end of the tube being connected to a source of pressurized air.

In a preferred embodiment of the present invention the device further includes a facemask configured to fit over at least the eyes and nose of the user and the strap secures the facemask to the face of the user.

According to further features in preferred embodiments of the invention described below, the source of pressurized air is the facemask or the air supply controller or the air supply mouthpiece.

According to another embodiment each of the ear portions of the air space includes a partition having an opening, the partition dividing the ear portion into a subspace adjacent the user's ear and a subspace removed from the user's ear, and wherein the first end of the tube is connected to the subspace removed from the user's ear.

The present invention successfully addresses the shortcomings of the presently known configurations by providing a simple and reliable device for facilitating the equalization of pressure across the user's eardrums which is particularly useful during undersea diving.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a diving device which can be used to equalize pressure across the eardrum.

The principles and operation of a device according to the present invention may be better understood with reference to the drawings and the accompanying description.

Figure 1:
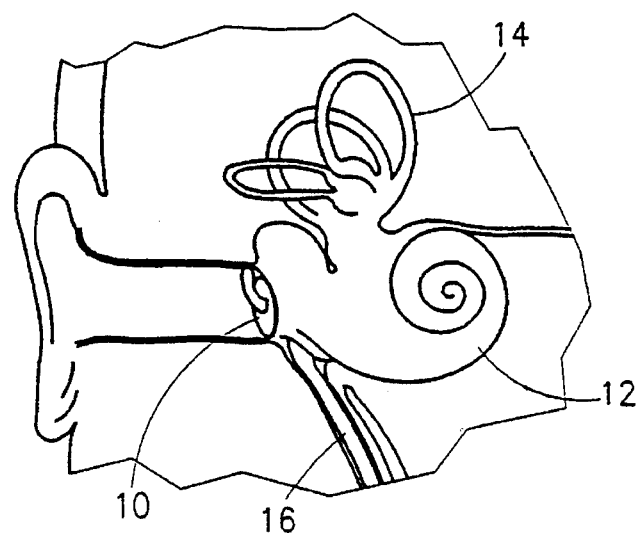
FIG. 1 is a cross-sectional view of the human ear.
Figure 2:
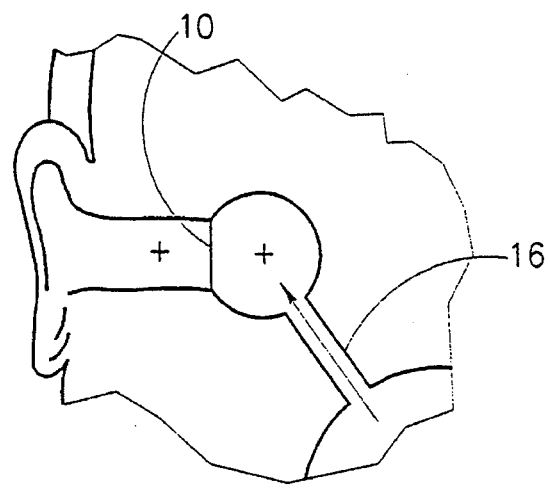
FIG. 2 is a schematic view of the human ear under pressure equalization.
Figure 3:
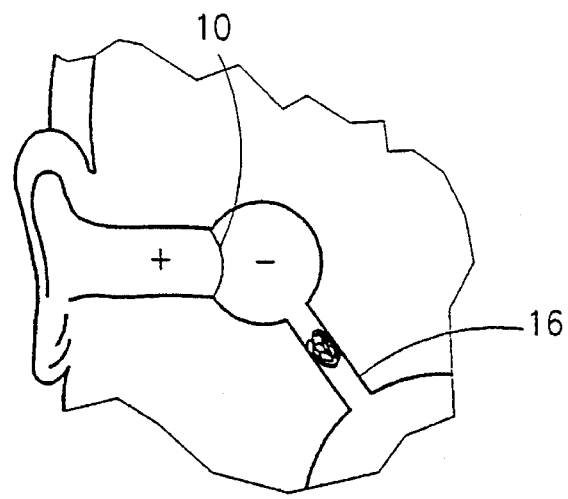
FIG. 3 is a schematic view of the human ear with a blocked eustachian tube which prevents pressure equalization.
Figure 4:
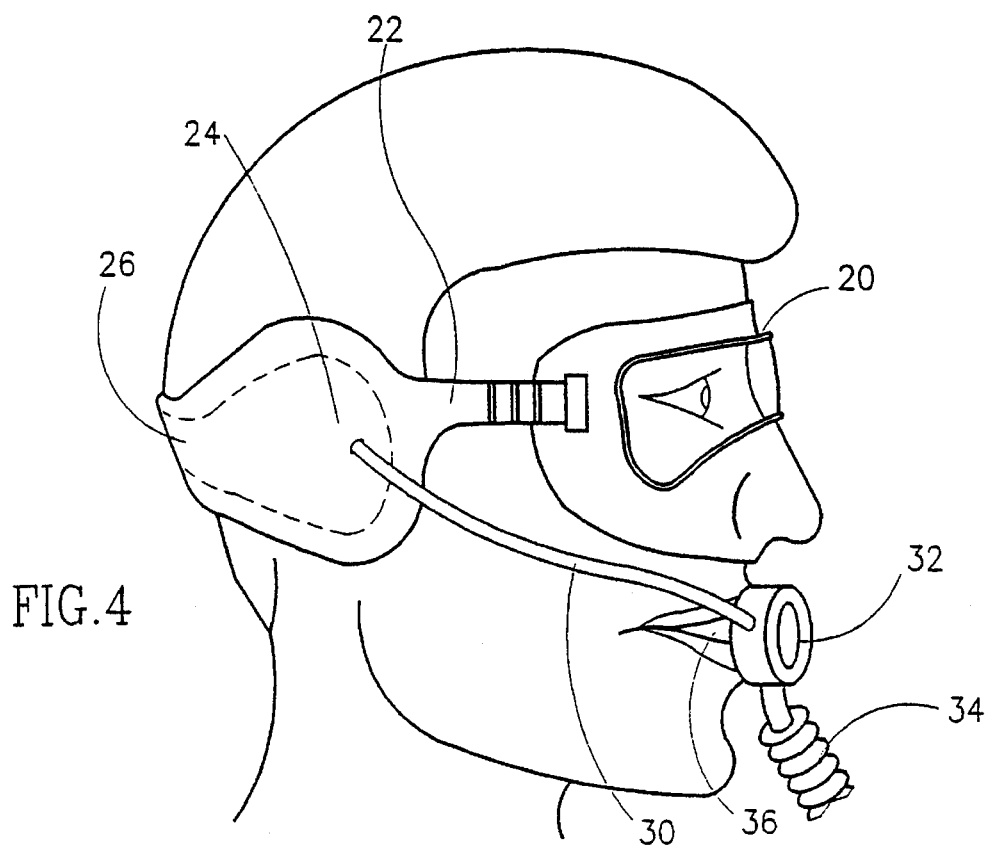
FIG. 4 shows one embodiment of a device according to the present invention with a tube connected to the air controller.

Referring now to the drawings, FIG. 4 depicts a basic embodiment of a device according to the present invention. In the preferred embodiments illustrated in the drawings, the device includes a facemask 20 which is configured to fit over at least the eyes and nose of the user.

Facemask 20 is secured to the face of the user using a strap 22. Strap 22 is configured such that, when secured to the head of the user, at least a portion of strap 22 is raised toward the center compared to the periphery so as to define a single air space between itself and the user's head.

It will be appreciated that whereas strap 22 is preferably secured to facemask 20, so that it serves both to retain facemask 20 and to equalize pressure in the ears of the user, strap 22 need not necessarily serve the former function. Thus, it may be desired in certain application to use a pressure equalization device according to the present invention without using a facemask at all or using a facemask which is secured to the head of the user through means ether than the pressure equalization strap.

Figure 7:
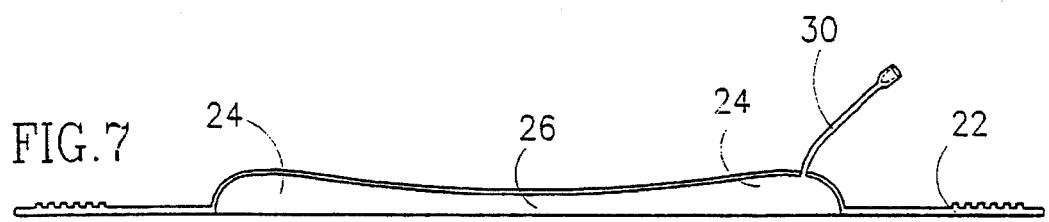
FIG. 7 is a side cross sectional view of a typical device according to the present invention.
Figure 8:
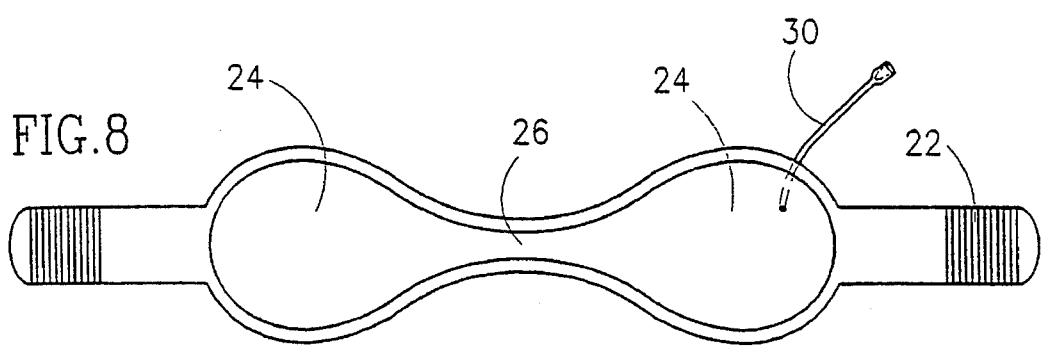
FIG. 8 is a plan view of the device of FIG. 7.

Strap 22 is shown in side and plan views in FIGS. 7 and 8, respectively. The air space defined by strap 22 includes a pair of ear portions 24 which overly the user's ears. The air space further includes a connecting portion 26 which overlies the sides and back of the user's head and which connects the two ear portions 24 together, serving to equalize the pressure between the two ears of the user. Preferably, ear portions 24 of the air space are somewhat raised and/or enlarged compared to connecting portion 26 of the air space as shown in FIG. 7. Preferably, too, at least a part of ear portions 24 is made of relatively thin flexible material so as to allow these members to serve as a diaphragm for transmitting ambient water pressure to the space defined by ear portions 24. The advantage of such a construction is that it makes it possible to take advantage of the ambient water pressure to fine-tune the pressure on the user's ear, a pressure which, in the absence of this fine-tuning, would be determined by the pressure provided by the mechanical pressure regulator. A further advantage of using a relatively thin flexible material for the ear portions 24 is that the use of such a thin diaphragm improves the diver's ability to hear underwater.

Finally, a device according to the present invention includes a tube 30 for supplying air to the air space. Preferably, only single tube 30 is used, although two or more tubes may also be used. The use of a single tube 30 is possible since the two ear portions 24 of the air space are connected to each other through connecting portion 26 so that tube 30 which may is connected to the air space at any point will adequately pressurize the entire air space, including both of the user's ears to substantially the same pressure.

Tube 30 has two ends. One of these is connected to the air space at some convenient point, while the second end is connected to a source of pressurized air, preferably at substantially the ambient pressure.

Figure 5:
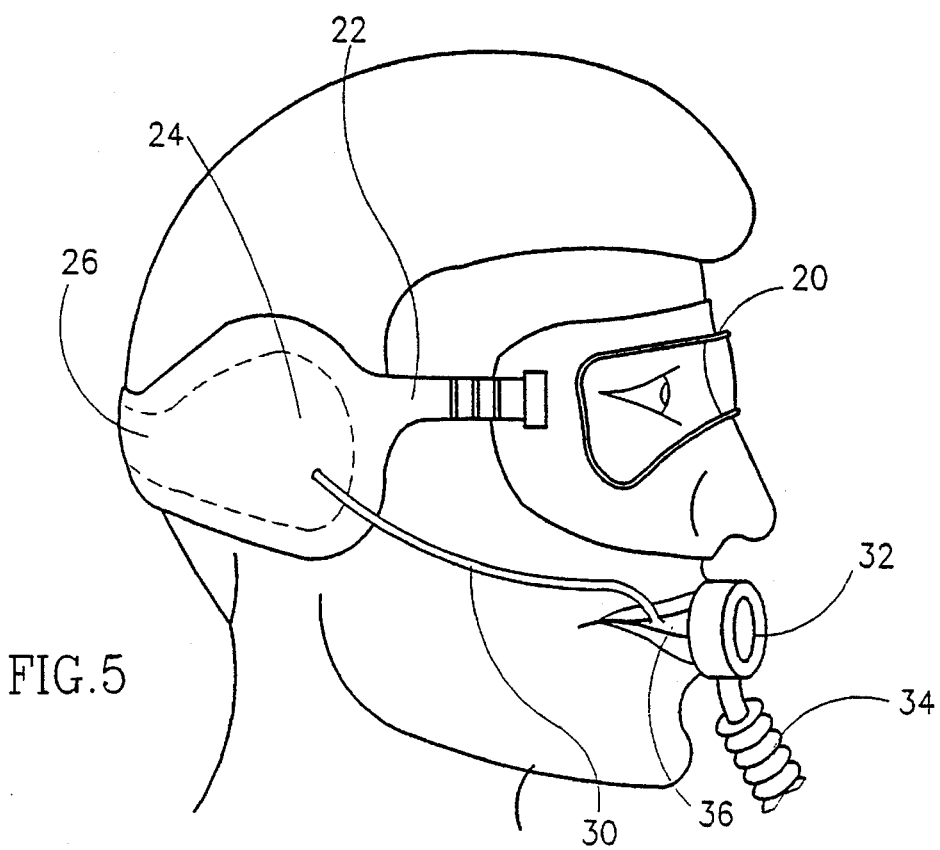
FIG. 5 shows one embodiment of a device according to the present invention with a tube connected to the breathing apparatus mouthpiece.
Figure 6:
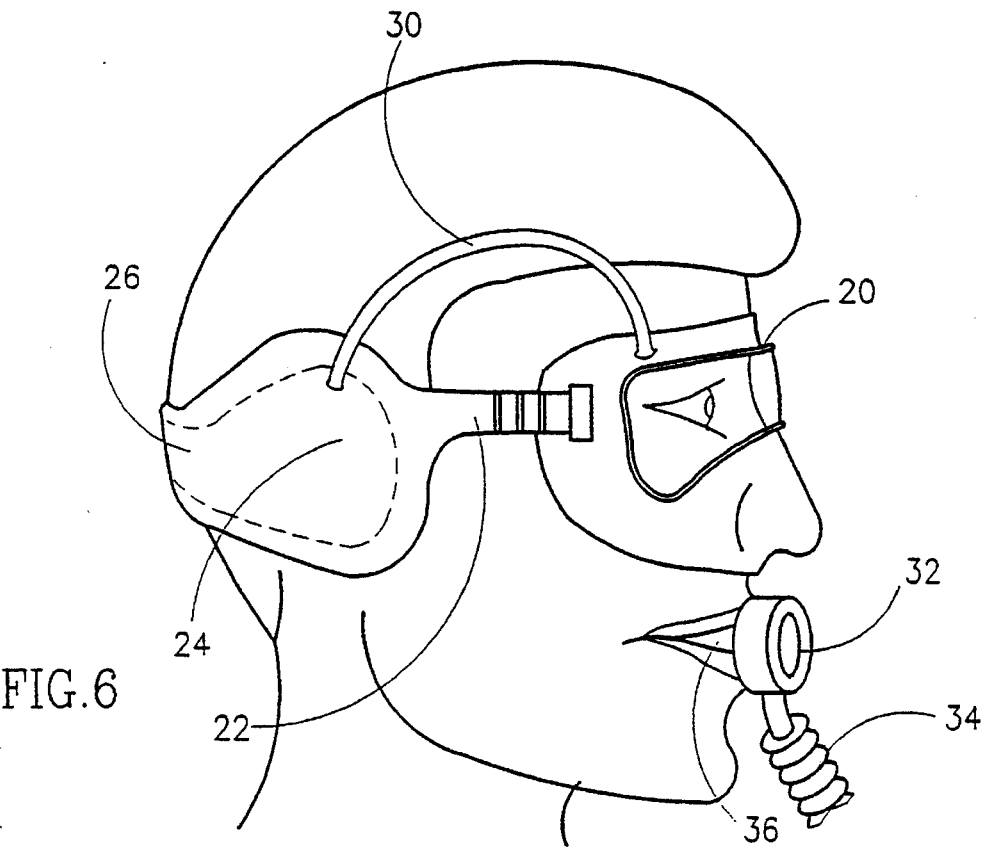
FIG. 6 shows one embodiment of a device according to the present invention with a tube connected to the face mask.

Shown in FIGS. 4–6 are three possible connections of the second end of tube 30 to a source of pressurized air. In FIG. 4, tube 30 is connected to the air supply controller 32 which reduces the pressure of the air coming from the air tanks (not shown) through air supply line 34 just prior to releasing the air to the mouthpiece 36 which is held in the use's mouth. In FIG. 5 tube 30 is connected directly to mouthpiece 36.

Figure 11:
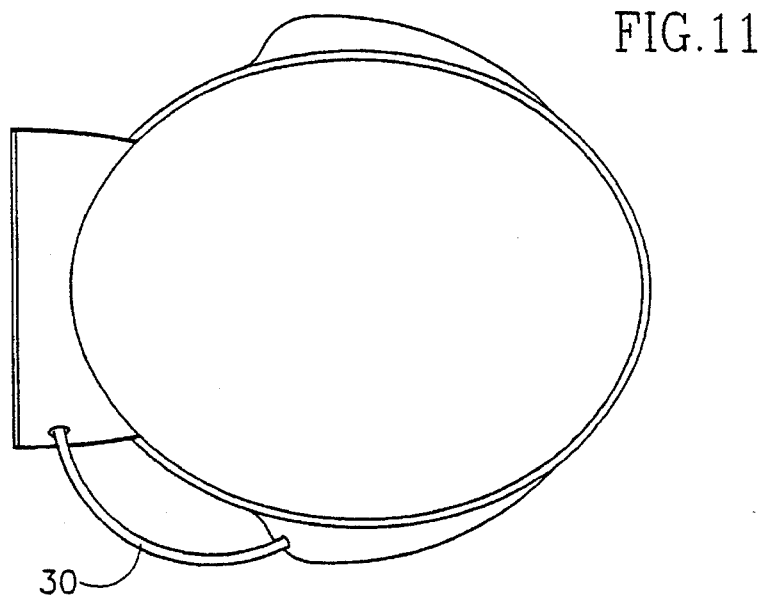
FIG. 11 is a top view of a device according to the present invention.

Shown in FIG. 6 is a configuration wherein the single tube 30 is connected to facemask 20. The pressure within facemask 20 is presumably near ambient since facemask 20 covers the user's nose which is connected to the user's mouth cavity which is being supplied through mouthpiece 36. Another view of the configuration of FIG. 6 is provided in FIG. 11 which is a top view of the device of FIG. 6.

Figures 9, 10:
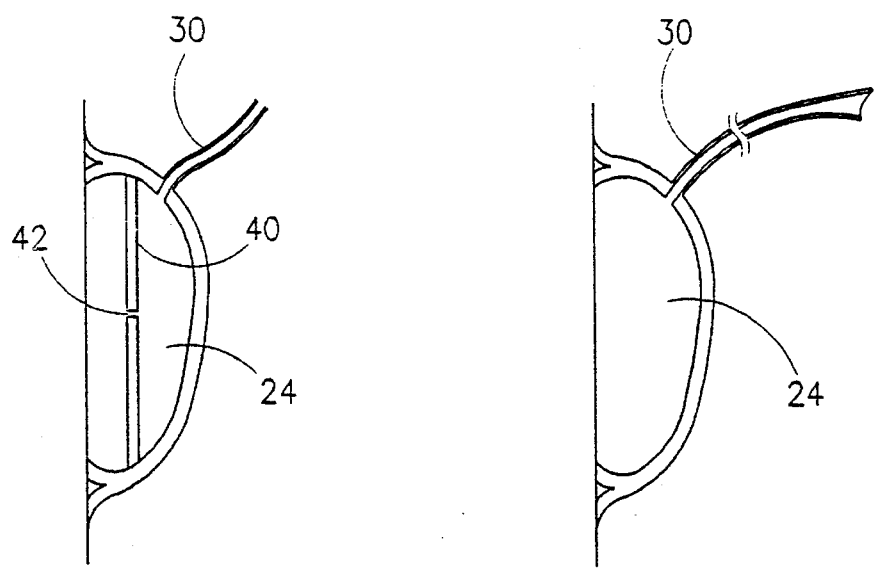
FIG. 9 is a side cross sectional view of the ear cap portion of a typical device according to the present invention.
FIG. 10 is a side cross sectional view of the ear cap portion of another embodiment of a typical device according to the present invention.

Shown in FIG. 9 is a side cross-sectional view of ear portion 24 of the air space. Preferably, the periphery of ear portion 24 which comes in contact with the user's head are flared as shown in FIG. 9 so as to provide a better seal and prevent the leakage of air from the air space or water into the air space.

The peripheral edge of strap 22 (depicted in FIG. 8) which contacts on the user's head is dimensioned for sealing the airspace against the user's head so as to prevent water from entering the airspace or air from leaving the airspace. Preferably, the peripheral edge is flared (FIGS. 9 and 10) in the direction of the user's head to provide a better seal of the airspace against the user's head.

Shown in FIG. 10 is an alternative embodiment of ear portion 24. Here, each ear portion 24 of the air space includes a partition 40 which features a small opening 42, Partition 40 divides ear portion 24 into two subspaces—one adjacent the user's ear and a second subspace which is removed from the user's ear. An end of tube 30 is connected to the subspace removed from the user's ear.

The purpose of partition 40 with its opening 42 is to retard in a controlled manner the increase in pressure in ear portion 24 of the air space. Retarding the pressure increase prevents temporary under-pressure condition in the middle ear which reduces or eliminates the edema and secretions of the mucous in the middle ear.

The size of opening 42 is selected so that the pressure in the subspace adjacent the user's ear does not rise instantaneously with increases in pressure in the removed subspaces but rather increases only gradually at a rate which is largely determined by the dimensions of opening 42.

While the invention has been described with respect to a limited number of embodiments, it will be appreciated that many variations, modifications and other applications of the invention may be made.

What is claimed is:

1. A device for facilitating the equalization of pressure across the eardrum of a user, comprising:
   (b) a strap, at least a portion of said strap, when said strap is secured to the head of the user, defining a single air space, said air space including ear portions overlying the user's ears and a connecting portion overlying the sides and back of the user's head and connecting said ear portions; and
   (c) a tube for supplying air to said air space, a first end of said tube being connected to said air space and a second end of said tube being connected to a source of pressurized air.

2. The device of claim 1, further comprising a facemask configured to fit over at least the eyes and nose of the user; wherein said strap secures said facemask to the face of the user.

3. The device of claim 1, wherein said air space is enlarged over the user's ears.

4. The device of claim 1, wherein said source of pressurized air is a facemask.

5. The device of claim 2, wherein said source of pressurized air is said facemask.

6. The device of claim 1, wherein said source of pressurized air is an air supply controller.

7. The device of claim 1, wherein said source of pressurized air is an air supply mouthpiece.

8. The device of claim 1, wherein each of said ear portions of said air space includes a partition having an opening, said partition dividing said ear portion into a subspace adjacent the user's ear and a subspace removed from the user's ear, and wherein said first end of said tube is connected to said subspace removed from the user's ear.

9. The device of claim 1, wherein at least a portion of said ear portions of said strap have a thickness which is smaller than an average thickness of said strap.

10. The device of claim 8, wherein at least a portion of said ear portions of said strap have a thickness which is smaller than an average thickness of said strap.

11. The device of claim 1, wherein said strap includes a peripheral edge for sealing against the user's head.

12. The device of claim 11, wherein at least a portion of said peripheral edge is flared in the direction of the user's head.

* * * * *